(12) United States Patent
Kennedy et al.

(10) Patent No.: US 6,710,066 B2
(45) Date of Patent: *Mar. 23, 2004

(54) PHOTOCHEMOTHERAPEUTIC METHOD USING 5-AMINOLEVULINIC ACID AND OTHER PRECURSORS OF ENDOGENOUS PORPHYRINS

(75) Inventors: James C. Kennedy, Kingston (CA); Roy H. Pottier, Kingston (CA)

(73) Assignee: Queen's University at Kingston, Kingston (CA)

( * ) Notice: Subject to any disclaimer, the term of this patent is extended or adjusted under 35 U.S.C. 154(b) by 24 days.

This patent is subject to a terminal disclaimer.

(21) Appl. No.: 09/816,329

(22) Filed: Mar. 26, 2001

(65) Prior Publication Data

US 2001/0021370 A1 Sep. 13, 2001

Related U.S. Application Data

(63) Continuation of application No. 09/293,835, filed on Apr. 19, 1999, which is a continuation-in-part of application No. 08/082,113, filed on Jun. 28, 1993, now Pat. No. 5,422,093, which is a continuation-in-part of application No. 07/865,151, filed on Apr. 8, 1992, now Pat. No. 5,234,940, which is a continuation-in-part of application No. 07/783,750, filed on Oct. 28, 1991, now Pat. No. 5,211,938, which is a continuation of application No. 07/386,414, filed on Jul. 28, 1989, now Pat. No. 5,079,262.

(51) Int. Cl.[7] .................. A61K 31/40; A61K 31/195
(52) U.S. Cl. .................. 514/410; 514/410; 514/561; 514/554; 514/557; 424/9.6; 424/9.61
(58) Field of Search .................. 514/554, 557, 514/561, 410; 424/9.6, 9.61

(56) References Cited

U.S. PATENT DOCUMENTS

| 4,772,681 A | 9/1988 | Fukuda et al. ............... 540/145 |
| 4,932,934 A | 6/1990 | Dougherty et al. ........... 604/21 |

(List continued on next page.)

FOREIGN PATENT DOCUMENTS

| EP | 0 233 701 | 8/1987 |
| WO | 91/01727 | 2/1991 |
| WO | 93/08715 | 5/1993 |
| WO | WO 93/20810 | 10/1993 |
| WO | WO 94/06424 | 3/1994 |
| WO | WO 94/12239 | 6/1994 |
| WO | WO 95/05813 | 3/1995 |
| WO | 95/07077 | 3/1995 |
| WO | WO 95/31189 | 11/1995 |

OTHER PUBLICATIONS

Boehncke, et al., Treatment of Psoriasis by Topical Photodynamic Therapy with Polychromatic Light, *The Lancet*, 343:801, Mar. 1994.

(List continued on next page.)

*Primary Examiner*—Russell Travers
*Assistant Examiner*—Shahnam Sharareh
(74) *Attorney, Agent, or Firm*—Beth A. Burrous; Foley & Lardner

(57) ABSTRACT

Methods of detecting and treating rapidly growing exogenous cells, such as Protista, or parasites, that preferentially accumulate a photoactivatable porphyrin in which 5-aminolevulinic acid or precursor thereof is administered to the patient, or contacted to the exogenous cells, in an amount sufficient to induce synthesis fluorescence and/or photosensitizing concentrations of a protoporphyrin IX in the exogenous cells, followed by exposure of the exogenous cells to light of photoactivating wavelengths.

15 Claims, 1 Drawing Sheet

U.S. PATENT DOCUMENTS

Figure 1:
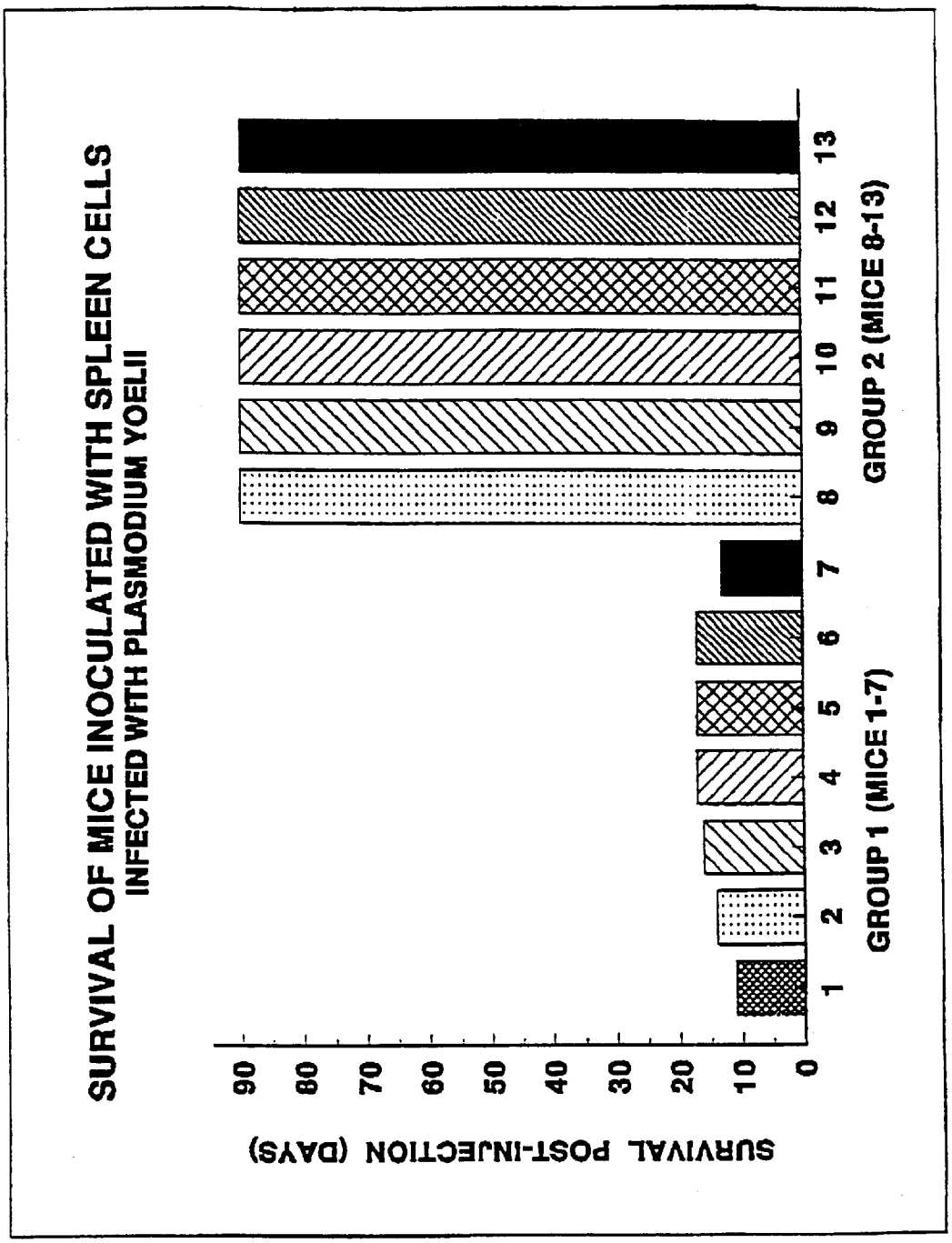

| | | | |
|---|---|---|---|
| 4,977,177 A | 12/1990 | Bommer et al. | 514/410 |
| 5,004,811 A | 4/1991 | Bommer et al. | 540/145 |
| 5,079,262 A | 1/1992 | Kennedy et al. | 514/561 |
| 5,127,938 A | 7/1992 | Rebeiz | 71/113 |
| 5,163,990 A | 11/1992 | Rebeiz | 71/70 |
| 5,200,427 A | 4/1993 | Rebeiz et al. | 514/561 |
| 5,211,938 A | 5/1993 | Kennedy et al. | 424/7.1 |
| 5,219,878 A | 6/1993 | Ringuet et al. | 514/414 |
| 5,226,907 A | 7/1993 | Tankovich | 606/133 |
| 5,234,940 A | 8/1993 | Kennedy et al. | 514/410 |
| 5,422,093 A | 6/1995 | Kennedy et al. | 424/9.61 |
| 5,423,803 A | 6/1995 | Tankovich et al. | 606/9 |
| 5,425,728 A | 6/1995 | Tankovich | 606/9 |
| 5,484,803 A | 1/1996 | Richter | 514/410 |
| 5,705,518 A * | 1/1998 | Richter et al. | 514/410 |
| 5,955,490 A | 9/1999 | Kennedy et al. | |

OTHER PUBLICATIONS

Fukuda et al., Photodynamic Action of Endogenously synthesized Porphyrins from Aminolevulinic . . . , Int. J. Biochem., 25:10; 1395–1398, 1993.

Loh et al., Endogenous Porphyrin Distribution–Induced by 5–Aminolaevulinic Acid . . . , J. Photochem. Photobiol., 20:47–54, 1993.

Van der Veen et al., In Vivo Fluorescence Kinetics and Photodynamic Therapy Using 5–Aminolaevulinic . . . , Br. J. Cancer, 70:867–872, 1994.

Grant et al., Photodynamic Therapy of Normal Rat Arteries After Photosensitisation Using . . . , Br. J. Cancer, 70:72–78, 1994.

German Abstract No. A78035910, "Investigation and Therapy in Dermatology with Dye Lasers", Anders et al., pp. 772, (1977).

Qian et al., "A Comparison of Different Photosensitizing Dyes with Respect to Uptake C3H–Tumors and Tissues of Mice", Cancer Letts., vol. 36:1–10, (1987).

Malik et al., "New Trends In Photobiology (Invited Review) Bactericidal Effects of Photoactivated Porphyrins—An Alternative Approach to Antimicrobial Drugs", Journal of Photochemistry and Photobiology, vol. 5:281–293, (1990).

Kennedy et al., "Topical Photodynamic Therapy for Cancers of the Skin", Canadian Dermatology Association Journal, vol. 5, No. 3, pp. 45–47, (1991).

Bickers et al., "Biosynthesis of Porphyrins in Mammalian Skin and In the Skin of Porphyric Patients", The Journal Investigative Dermotology, vol. 68:5–9, (1977).

Malik et al., "5–Aminolevulinic Acid Stimulation of Porphyrin and Hemoglobin Synthesis by Uninduced Friend Erythroleukemic Cells", Cell Differentiation, vol. 8:223–233, (1979).

Malik et al., "Destruction of Erythroleukaemic Cells By Photoactivation of Endogenous Porphyrins", Br. J. Cancer, vol. 56:589–595, (1987).

Malik et al., "The Role of Hemin in the Regulation of Heme Synthesis by Fetal Mouse Liver Erythroblasts In Culture", Exp. Hemat., vol. 7, No. 4, pp. 183–188, (1979).

Malik et al., "Regulation of Hemoglobin Synthesis, Iron Metabolism, and Maturation of Friend Leukemic Cells by 5–Amino Levulinic Acid and Hemin", Differentiation, vol. 13:71–79, (1979).

Malik et al., "Inactivation of Erythrocytic, Lymphocytic and Myelocytic Leukemic Cells By Photoexcitation of Endogenous Porphyrins", Journal of Photochemistry and Photobiology: Biology, vol. 4:195–205, (1989).

Hanania et al., "The Effect of EDTA and Serum on Endogenous Porphyrin Accumulation and Photodynamic Sensitization of Human K562 Leukemic Cells", Cancer Letters, vol. 65:127–131, (1992).

Sima et al., "Experimental Porphyric Neuropathy: A Preliminary Report", Canada J. Neurol. Sci., vol. 8, No. 2, pp. 105–114, (1981).

Kennedy et al., "Endogenous Proptoporphyrin IX, A Clinically Useful Photosensitizer for Photodynamic Therapy", J. Photochem. Photobiol. B: Biol., vol. 14:275–292, (1992).

Shizheng et al., "Endogenous Porphyrins in Murine Skin and Transplanted PAM–212 Squamous Cell Carcinoma Tissues after Injection of δ–Aminolevulinic Acid", Chinese Medical Journal, vol. 108(4):286–290, (1995).

Yang et al., "Treatment with 5–Aminolevulinic Acid and Photoactivating Light Causes Destruction of Preimplantation Mouse Embryos", Fertility and Sterility, vol. 63(5):1088–1093, (1995).

Hua et al., "Effectiveness of δ–Aminolevulinic Acid–Induced Protoporphyrin as a Photosensitizer—For Photodynamic Therapy In Vivo", Cancer Research, vol. 55:1723–1731, (1995).

Ash et al., "New Drugs and Future Developments in Photodynamic Therapy", Eur. J. Cancer, vol. 29A(12):1781–1783, (1993).

Koenig et al., "In Vivo Photoproduct Formation During PDT with ALA–Induced Endogenous Porphyrins", J. Photochem. Photobiol. B: Biol., vol. 18:287–290, (1993).

Van Hillegersberg et al., "Current Status of Photodynamic Therapy in Oncology", Drugs, vol. 48(4):510–527, (1994).

Yang et al., "Photodynamic Ablation of Early Pregnancy in the Rat with 5–Aminolevulinic Acid: A Potential New Therapy for Tubal Ectopic Pregnancy in the Human", Fertility and Sterility, vol. 62(5):1060–1065, (1994).

Wolf et al., "Photodynamic Therapy for Mycosis Fungoides after Topical Photosensitization with 5–Aminolevulinic Acid", Journal of the American Academy of Dermatology, vol. 31:678–680, (1994).

Fukuda et al., "Tumor–Localizing Properties of Porphyrins, In vitro Studies Using the Porphyrin Precursor, Aminolevulinic Acid, In Free and Liposome Encapsulated Forms", Drug Des. Deliv., vol.5:133–139, (1989).

Yang et al., "Intrauterine 5–Aminolevulinic Acid Induces Selective Fluorescence and Photodynamic Ablation of the Rat Endometrium", Photochemistry and Photobiology, vol. 57(5):803–807, (1993).

Grant et al., "Photodynamic Therapy of Oral Cancer: Photosensitisation with Systemic Aminolaevulinic Acid", The Lancet, vol. 342:147–148, (1993).

Loh et al., "Oral Versus Intravenous Administration of 5–Aminolaevulinic Acid for Photodynamic Therapy", Br. J. Cancer, vol. 68:41–51, (1993).

Charlesworth et al., "The Use of 5–Aminolevulinic Acid (ALA) In Photodynamic Therapy (PDT)", News and Views, vol. 18:99–100, (1993).

Kennedy, "Photochemotherapy—Clinical Aspects", Department of Oncology and Pathology, Photosensitisation. Edited by G. Moreno et al., pp. 453–463, (1988).

Kennedy, "Photodynamic Therapy with Endogenous Protoporphyrin IX: Basic Principles and Present Clinical Experience", Journal of Photochemistry and Photobiology, B: Biology, vol. 6:143–148, (1990).

Dennis et al., "Protection of NIH 3T3 Cells from Infection by Trypomastigotes and Sphaeromastigotes of J. Trypanosoma Cruzi, Telahuen Strain, by Porphyrins in the Presence and Absence of Light (630 and 690 NM)", *Parasitol.*, vol. 75(6):970–976, (1989).

Berlin et al., "Normal Pathways, Studied with the Aid of N", *The Metabolism of δ–Aminolaevulic Acid*, vol.64:80–99, (1956).

Brault et al., "Fundamental Aspects In Tumor Photochemotherapy: Interactions of Porphyrins with Membrane Model Systems and Cells", *Biochimie*, vol. 68:913–921, (1986).

Divaris et al., "Phototoxic Damage to Sebaceous Glands and Hair Follicles of Mice After Systemic Journal Administration of 5–Aminolevulinic Acid Correlates with Localized Protoporphyrin IX Fluorescence", *American of Patbology*, vol. 136(4):891–897, (1990).

Grossman, "PDT For Hirsutiem", *Lasers Surg. Med. Suppl.*, vol. 7:A205, (1995).

Malik et al., "Topical Application of 5–Aminolevulinic Acid, DMSO and EDTA: Protoporphyrin IX Accumulation in Skin and Tumours of Mice", *Journal of Photochemistry and Photobiology B: Biology*, vol. 28:213–218, (1995).

Korell et al., "Einsatz der Photodynamischen Lasertherapie in der Gynaekologie", *Gynaekol Geburtshilfliche Rundsch*, vol. 35:90–97, (1995).

Untch et al., "Synergistischer Effekt von Delta–Aminolaevulinsaeure und Photodynamischer Lasertherapie Anhand Eines In–Vitro–Modells Mit Dem ATP–Tumorchemosensitivitaetstest", *Gynaekol Geburtshilfliche Rundsch*, vol. 35:85–89, (1995).

Szeimies et al., "Topische Photodynamische Therapie In Der Behandlung Oberflaechlicher Hauttumoren", *Hautarzt*, vol. 46:315–318, (1995).

Wolf et al., "Photodynamic Therapy with 5–Aminolevulinic Acid:A Promising Concept for the Treatment of Cutaneous Tumors", *Dermatology*, vol. 190:183–185, (1995).

Yang, et al., "Evidence of Lasting Functional Destruction of the Rat Endometrium After 5–Aminolevulinic Acid Induced Photodynamic Ablation: Prevention of Implantation", *Am. J. Obstet. Gynecol.*, vol. 168(3):995–1001, (1993).

Wolf, et al., "Topical Photodynamic Therapy with Endogenous Porphyrins after Application of 5–Aminolevulinic Acid", *J. Am. Acad. Dermatol.*, vol. 28:17–21 (1993).

Goff et al., "Effects of Photodynamic Therapy with Topical Application of 5–Aminolevulinic Acid On Normal Skin of Hairless Guinea Pigs", *J. Photochem. Photobiol. B: Biol.*, vol. 15:239–251, (1992).

Peng et al., "Distribution and Photosensitizing Efficiency of Porphyrins Induced by Application of Exogenous 5–Aminolevulinic Acid in Mice Bearing Mammary Carcinoma", *Int. J. Cancer*, vol. 52:433–443, (1992).

Surolia et al., "De Novo Biosynthesis of Heme Offers a New Chemotherapeutic Target in the Human Malarial Parasite", *Biochemical and Biophysical Research Communications*, vol. 187(2):744–750, (1992).

Van Hillegersberg et al., "Selective Accumulation of Endogenously Produced Porphyrins in a Liver Metastasis Model in Rates", *Gastroenterology*, vol. 103:647–651, (1992).

Fukuda et al., "Tumor–Localizing Properties of Porphyrins in vivo Studies Using Free and Liposome Encapsulated Aminolevulinic Acid", *Comp. Biochem. Physiol.*, vol. 102B(2):433–436, (1992).

Bedwell et al., "Fluorescence Distribution and Photodynamic Effect of ALA–Induced PP IX in the DMH Rat Colonic Tunour Model", *Br. J. Cancer*, vol. 65:818–824, (1992).

Rebeiz et al., "Photodestruction of Tumor Cells By Induction of Endogenous Accumulation of Protoporphyrin IX: Enhancement By 1, 10–Phenanthroline", *Photochemistry and Photobiology*, vol. 55(3):431–435, (1992).

Andreoni et al., "Effects of HpD and Laser On Transformed and Corresponding Normal Cultured Cells: Diiferential Cytoxicity As An In Vitro Model For Tumor Photochemotherapy", *Porphyrins in Tumor Phototherapy*, pp. 143–155, (1993).

Robino et al. "Porphyrin Metabolism in Human Neoplastic Tissues", *Panminerva Medica*, pp. 290–292.

Samsoen M., Arsenal Medicamenteux Dermatologique, pp. 603–606, ISSN. 0752–5370 (1995) (Abstract).

Pottier et al., "Non–Invasive Technique for Obtaining Fluorescence Excitation and Emission Spectra In Vivo" *Photochemistry and Photobiology*, vol. 44, No. 5, pp. 679–687, (1986).

N. Navone, et al., Porphyrin biosynthesis in human breast cancer. Preliminary mimetic in vitro studies, *Med. Sci. Res.*, 1988; 16, 61–62, Buenos Aires, Republica Argentina.

* cited by examiner

PHOTOCHEMOTHERAPEUTIC METHOD USING 5-AMINOLEVULINIC ACID AND OTHER PRECURSORS OF ENDOGENOUS PORPHYRINS

CROSS REFERENCE TO RELATED APPLICATIONS

This application is a continuation of U.S. application Ser. No. 09/293,835, filed Apr. 19, 1999, which in turn is a continuation-in-part of U.S. application Ser. No. 08/082,113, filed Jun. 28, 1993, (now U.S. Pat. No. 5,422,093, issued Jun. 6, 1995), which is a continuation-in-part in U.S. application Ser. No. 07/865,151, filed Apr. 8, 1992, (now U.S. Pat. No. 5,234,940, issued Aug. 10, 1993), which is a continuation-in-part of U.S. application Ser. No. 07/783,750, filed Oct. 28, 1991 (now U.S. Pat. No. 5,211,938, issued May 18, 1993), which is a continuation of U.S. patent application Ser. No. 07/386,414, filed Jul. 28, 1989 (now U.S. Pat. No. 5,079,262, issued Jan. 7, 1992). The disclosures of all these applications are incorporated herein by reference.

FIELD OF INVENTION

This invention relates to the detection and treatment, by induced fluorescence and photochemotherapy, respectively, of certain tissue abnormalities (both cancerous and non-malignant of endogenous and exogenous origin), hyperproliferative cells, and normal cells. The invention also relates to the detection and treatment of abnormalities in body fluids or suspensions of tissues containing abnormal cells by induced fluorescence and photochemotherapy.

BACKGROUND OF INVENTION

Tissue abnormalities involving the skin usually are detected and assessed by a combination of visual inspection and palpation. In certain clinical situations the sensitivity of the visual inspection can be enhanced by the use of non-white light (either ultraviolet or a narrow band in the visible), or by the prior application of a contrast-enhancing agent such as dilute acetic acid or certain stains. Tissues abnormalities that involve surfaces that cannot be palpated (such as the bronchi or the urinary bladder) may be visualized via an appropriate scope. Some specialized scopes can detect induced fluorescence. If the abnormality in question is associated with a difference in either the extent or the pattern of tissue vascularization, such a scope may be used to determine the limits of the area involved by the abnormality, by visualizing an injected bolus of fluorescein or other fluorescent material as it passes through the vasculature of both the lesion and the adjacent normal tissue.

In addition, fluorescence-detecting scopes are being used experimentally to identify areas of tissue that show strong porphyrin fluorescence following the intravenous injection of exogenous porphyrins such as hematophorphyrin IX (HpIX), hematoporphyrin derivative (HpD), or "dihematoporphyrin ether". Such porphyrins tend to accumulate semi-preferentially in malignant tissues, but they also accumulate in tissues that are regenerating following an injury or in the rapidly growing tissues of an embryo or fetus. Normal liver, spleen, and kidney also tend to accumulate these porphyrins. Using such compounds and fluorescence-detecting scopes, areas of malignant tissue too small to be identified by standard forms of visual inspection have been identified in the bronchi and in the urinary bladder.

Unfortunately, a clinically significant (photosensitizing) amount of porphyrin may persist in the skin for at least two weeks, (occasionally for more than two months) following the intravenous injection of HpIX, HpD, or a semi-puridied preparation of HpD, such as Photofrin II. (Photophrin is a registered trademark of Quadra Logics, Inc. Vancouver, British Columbia, Canada.) This means that patients must avoid exposure to sunlight (either direct, or through window glass) for an inconveniently long period of time post-injection. Understandably, patient compliance often is poor, and accidental phototoxic "sunburn" is a common occurrence in the weeks following a diagnostic or therapeutic injection of porphyrin. Persistent photosensitivity is the major hazard associated with this technique, and is the main reason why it is not used more widely.

The standard treatments for cancer comprise surgery, radiotherapy and chemotherapy. However, other forms of treatment are also known, including photochemotherapy or photodynamic therapy (PDT), based on the discovery made over 90 years ago that unicellular organisms, i.e., certain rapidly growing cells (such as cells of the Lower Kingdom, now referred to as Protista), treated with certain chemicals will die when exposed to light. Thus, synthetic porphyrins have been shown in vitro to protect cells from infections such as parasites, e.g., tyromastigotes and sphaeromastigotes of *Tyropanosoma cruzi*, J. Parasitol., 75(6) 1989, p. 970–976, and gram positive bacteria, mycoplasma and yeasts, Malik et al. J. Photochemistry and Photobiology, B. Biology 5 281–293 (1990). *P. acne* is known to, in vitro, produce intracellular protoporphyrin in the presence of exogenous ALA. Kjeldstad, *Conference on Photosensitization and Photochemotherapy of Cancer*, Det Norske Videnskaps-Akademi, Mar. 16–17, 1993, Oslo, Norway.

PDT is currently being used, on an experimental basis, to treat several different types of cancer as well as certain non-malignant lesions such as psoriasis. The patient is given a photo-activatable drug that has some degree of specificity for the tissue being treated. A tissue volume that includes the target tissue is then exposed to photoactivating light so as to destroy the target tissue while causing only mild and reversible damage to the other tissues in the same treatment volume.

There are two main types of photochemotherapeutic agents in clinical use at present. The first type, methoxypsoralens, are given systemically. Ultraviolet light is essential to activate them. Localized exposure of psoralen-containing tissues to ultraviolet light induces a localized photochemical reaction that causes the drug to bind covalently to the DNA of living cells, thus destroying their proliferative potential. The second type, porphyrins and related photosensitizers, are also given systemically (by intravenous injection), although occasionally they are given either topically or by intralesional injection. They can be activated by visible (red) light. The localized exposure of porphyrin-containing tissues to such light ordinarily does not induce a chemical reaction between cell components and the porphyrin molecules. Instead, the porphyrins act as catalysts by trapping the energy of the photoactivating light and then passing it on to molecules of oxygen, which in turn are raised to an excited state that is capable of oxidizing adjacent molecules or structures. Cell death is not caused primarily by damage to the DNA, but by damage to essential membrane structures. The goal of photochemotherapy is sometimes cure (mainly for basal cell carcinomas), but usually the goal is palliation through local control when none of the standard forms of therapy are considered likely to offer a significant degree of benefit to the patient.

Methoxypsoralen (PUVA) therapy is used mainly for the treatment of psoriasis, but sometimes it is also used to treat very superficial cancers that involve the skin (mainly mycosis fungoides). However, there are two serious problems with such treatments. First, the procedure has been demonstrated in humans to be carcinogenic. Second, the depth at which malignant tissue can be killed is limited to a few millimeters below the illuminated surface. These problems severely limit the usefulness of the methoxypsoralens for photochemotherapy.

5-Amino-4-oxopentanoic acid, also known as 5-aminolevulinic acid and as *-aminolevulinic acid ("ALA") has been described in the cross referenced patents and patent applications first set forth in this specification for detecting and treating rapidly growing cells. ALA has also been reported for use in attenuating the growth and killing plants and insects when applied directly to such organisms followed by exposure to light, based on work of Rebeiz et al.

Synthetic porphyrins have also been used as photochemotherapeutic agents in treating rapidly growing, e.g. rapidly dividing or rapidly metabolizing infectious cells, such as infectious pathogens, including protozoal parasites, such as *Plasmodium falciparium* (which causes malaria in humans), various other species of Plasmodia, Leishmania, and amoebae, pathogenic fungi, and microplasma, including the various parasitic forms, all such cells and organisms being referred to herein as Protista. The term Protista as used here and in the literature refers to the lowest orders of the animal and vegetable kingdoms, single celled or collections of single celled organisms including: the eukaryotes, including protozoa, fungi and algae, and the prokaryotes, which are bacteria and blue-green algae.

At present, the porphyrins most commonly used for photochemotherapy are Hematoporphyrin IX (HpIX), Hematoporphyrin derivative (HpD) and various semi-purified preparations of HpD such as commercially available Photofrin® II, a semi-purified form of HpD. When porphyrins are used as photosensitizers, cell death results from damage to cell membranes. Consequently, malignant transformation is not a serious problem. Moreover, since the visible (red) light that is used to photoactivate porphyrins penetrates tissue much more deeply than does the ultraviolet light that must be used to photoactivate methoxypsoralens, the depth at which porphyrin-treated tissue can be killed is substantially greater. Also, since certain types of porphyrins show a significant tendency to accumulate preferentially in malignant tissues, it is sometimes possible to destroy malignant tissue without causing clinically significant damage to adjacent normal tissues.

The main problem with the systemic use of HpIX, HpD and Photofrin II is that photosensitizing concentrations persist in the skin for several weeks to several months following their administration. Consequently, severe accidental phototoxic skin reactions may occur unless the patient avoids exposure to sunlight (either direct, or filtered through window glass) until the concentration of the photosensitizer in the skin has been reduced to a harmless level. At present, the problem of photosensitivity following the administration of porphyrins is handled by advising the patient to avoid any form of exposure to sunlight (or to very bright artificial lights) for a period of at least two weeks post-injection, and to initiate subsequent exposure to sunlight very cautiously. Not all patients comply with these instructions, since it often is quite inconvenient to do so. In addition, the use of a sunscreen with a high blocking factor is recommended with warning that this will only reduce the hazard somewhat, not eliminate it completely. In a few cases, patients whose photosensitization persisted for more than a month post-treatment have been given large daily doses of beta-carotene over a period of several months in an attempt to prevent accidental phototoxic damage. Finally, attempts have been made to reduce phototoxicity by applying the photosensitizer topically to a limited area.

However, another type of problem is encountered if HpIX or HpD is applied topically in DMSO (dimethylsulfoxide), Azone, or some other vehicle intended to enhance their diffusion through tissue. The porphyrins tend to become immobilized wherever they happened to be when the DMSO or Azone becomes diluted by normal tissue fluids to such an extent that the porphyrins can no longer diffuse through the tissue (or even remain in solution). Consequently, the topical application of porphyrins often is associated with a loss of specificity for malignant tissues, and normal tissues near the site of application may develop persistent photosensitization from the localized concentration of porphyrin.

OBJECT OF INVENTION

It is an object of the present invention to provide a method for the detection of certain types of malignant and non-malignant cells including a collection of cells, and tissue abnormalities by induced fluorescence.

It is yet another object of this invention to provide a photodynamic (photosynthesizing) treatment method using an agent which can be administered either systemically or topically which is not in itself a photosensitizer but which induces the synthesis or accumulation or both of protoporphyrin IX (PpIX) and other endogenous porphyrins, their precursors and their photoproducts, in rapidly growing cells, including abnormal cells in otherwise normal tissues, in vivo or in vitro.

The terms porphyrin(s) and their precursors refer to compounds produced in vivo in the synthesis of heme and other endogenously produced photoactivatable compounds including their photoproducts.

SUMMARY OF INVENTION

This invention is based on the finding that exogenously administered ALA and other precursors of PpIX are metabolized in patients to PpIX and that PpIX preferentially accumulates in rapidly growing cells, as contrasted with less rapidly growing cells. The rapid growth is correlated with the metabolic activity, so that the differential accumulation is affected by the relative metabolic activity between different cells.

This invention provides a method for detecting in a patient, a malignant or non-malignant lesion or abnormality which is sensitive to PpIX, namely those which preferentially accumulate PpIX, comprising administering to said patient an effective amount of a precursor of PpIX in the biosynthetic pathway for heme so as to induce an accumulation of PpIX in said lesions, and exposing said lesions to light having a wavelength within the absorption spectrum of said PpIX, thereby to induce fluorescence in said lesions.

Another aspect of this invention is a method for treating malignant and non-malignant hyperproliferative lesions of the skin, mucosa, endometrium and urothelium which are sensitive to PpIX in a patient, comprising administering to said patient an effective amount of a precursor of PpIX in the biosynthetic pathway for heme so as to induce synthesis or accumulation or both of PpIX or other endogenous porphyrins, their precursors and their photoproducts in said lesions, and exposing said lesions to light having a wavelength within the photoactivating action spectrum of said PpIX to thereby induce photoactivation in said lesions.

Thus, the rapidly growing cells involved can be either malignant or non-malignant hyperproliferative cells. The hyperproliferative cells can be normal, rapidly growing cells or abnormal cells in otherwise normal tissue. The abnormal cells in an otherwise normal tissue can include abnormal rapidly growing cells endogenous to the patient or abnormal, rapidly growing cells which are exogenous to the patient. These rapidly growing cells that are exogenous to the patient shall, for convenience, be referred to hereby, depending on the degree of generality, as rapidly growing exogenous cells, rapidly growing Protista cells and rapidly growing parasite cells.

One aspect of this invention is induction in vivo or in vitro of the biosynthesis and selective accumulation of fluorescing or photosensitizing concentrations of protoporphyrin IX or other endogenous porphyrins such as coproporphyrin I, coproporphyrin III, uroporphyrin I, uroporphyrin III, or fluorescent metalloporphrins such as zinc protoporphyrin IX in Protista and parasites of humans or other animals, by exposing said Protista and endogenous cells under appropriate conditions in vivo or in vitro to an effective concentration of 5-aminolevulinic acid or other precursor of said porphryin(s) in the biosynthetic pathway for heme.

Still another aspect of this invention is the detection or enumeration of Protista and parasites of humans or other animals, by inducing in vivo or in vitro (ex vivo) the biosynthesis and selective accumulation of fluorescing concentrations of protoporphyrin IX or other endogenous porphyrin in the parasites as described previously, and then using such fluorescence to detect, enumerate, or otherwise quantify said Protista and parasites.

Yet another aspect of this invention is the selective killing of Protista and parasites of humans or other animals in vivo or in vitro, by inducing the biosynthesis and selective accumulation of photosensitizing concentrations of protoporphyrin IX or other endogenous porphyrin in the Protista or endogenous cells as described above, and then exposing the photosensitized parasites to an effective dose of light of wavelengths lying within the photoactivation spectrum of said porphyrin(s) or of photosensitizing photoproducts of said porphyrin(s) that may be produced during said exposure.

By another aspect of this invention there is provided use of a composition comprising a precursor of protoporphyrin IX in the biosynthetic pathway for heme for the manufacture of a medicament for treating malignant and non-malignant tissue abnormalities and lesions.

In preferred aspects of this invention the preferred precursor of protoporphyrin IX is 5-amino-4-oxo-pentanoic acid, otherwise known as 5-aminolevulinic acid, and a preferred wavelength of the photoactivating light is in the range of 625 to 670 nm, more preferably a red light of 625 to 640 nm.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE DRAWING

FIG. 1 illustrates the duration of survival of individual mice following the injection of spleen cells infected with *P. yoelii*. Group (1) mice were given spleen cells that had been exposed to ALA in vivo by then kept in the dark. The average survival of the recipients of these cells was 15 days. Group (2) mice were given the same number of cells from the same cell suspension after it had been exposed to photoactivating light. All of these mice remained in good health for 90 days, at which time the experiment was terminated.

DETAILED DESCRIPTION OF PREFERRED EMBODIMENT

Protoporphyrin IX (PpIX), a naturally occurring photosensitizer, is the immediate precursor of heme in the heme biosynthetic pathway. All nucleated cells have at least a minimal capacity to synthesize PpIX, since heme is necessary for the synthesis of various essential heme-containing enzymes. Certain types of cells and tissues can synthesize relatively large quantities of PpIX. Under normal conditions, the synthesis of PpIX in such tissues is under such tight feed-back control that the cells produce it at a rate just sufficient to match their need for heme. However, the usual rate-limiting step in the process, the synthesis of 5-aminolevulinic acid, can be bypassed by the provision of exogenous ALA, porphobilinogen, or other precursor of PpIX. Certain tissues and organs will then accumulate such a large excess of PpIX that they become both fluorescent and photosensitive. At least in the case of the skin, the PpIX appears to be synthesized in situ. ALA, which is commercially available from Sigma Chemical Company and other sources and which is water soluble, can be administered orally, topically or by injection. The oral and parenteral routes lead to the induction of clinically useful concentrations of PpIX in certain benign and malignant tissues throughout the body. Only certain types of tissue synthesize and accumulate clinically useful amounts of PpIX when provided with an excess of ALA. By the expression "rapidly growing cell" is meant herein any lesion, abnormal cell or normal cell that exhibits cell growth substantially greater than that of the surrounding tissues and that preferentially accumulates protoporphyrin IX from exogenous ALA. Thus, the cells include rapidly growing cells that are endogenous to the patient and rapidly growing exogenous cells such as Protista and parasite cells. The term "rapidly growing cells" is also used here to include living, metabolically active cells as contrasted with metabolically inactive (dead or dormant) cells such as found in the malarial applications of this invention.

At the present time, treatment of basal cell, basosquamous and squamous cell carcinomas and other lesions of the skin, mucosa (respiratory, digestive, and vaginal), endometrium and urothelium is contemplated. Sites, which could include lesions or cellular abnormalities, generally are those of epithelial or endothelial origin including but not limited to those involving (i) skin, circulatory system and conjunctiva; (ii) the lining of the mouth, pharynx, esophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tissues or suspensions of body fluids containing abnormal cells, including blood, that can be made accessible to photoactivating light either in vitro, at time of surgery, in vivo through the skin via surface irradiation or via an optical fibre inserted through a needle; (x) all exocrine glands and associated ducts, including: mammary glands, sebaceous glands, ceruminous glands, sweat glands, and lacrimal glands; mucus-secreting glands of the digestive, urogenital, and respiratory systems; salivary glands; liver, bile ducts, and gall bladder; pancreas (exocrine component); gastric and intestinal glands; prostate; Cowper's, Bartholin's and similar glands. It is also contemplated that cell abnormalities in the gonads (testes and ovaries), thymus, spleen, lymph nodes, bone marrow, lymph and blood would also be treated according to the invention. Tumors of the nervous system or connective tissues (sarcomas) would also be treated according to this invention.

Treatment of non-malignant lesions such as genital warts and psoriasis and of endometrial tissues for indications such as contraception, vaginal bleeding and endometriosis is also contemplated.

As used herein the term "skin" includes:

(A) the covering of the external surface of most of the body, commonly termed the skin.

(B) the covering of the external genitalia:
  labia majora, labia minora, clitoris, and
  glans penis, prepuce, and associated (C) the covering of the zone of transition between skin and the mucosa of the digestive system:
  anal verge
  vermillion border of the lips (D) the lining of the external auditory meatus, and the covering of the external surface of the tympanic membrane (E) all exocrine glands and associated ducts that are located at least partially within an epidermal surface described above, or within the underlying dermis, such as the pilosebaceous units of the skin.

The term "mucosa" includes:

(A) the lining of the whole of the respiratory tract:
  nasal passages and nasal sinuses
  nasal pharynx and associated structures
  larynx, vocal cords, and associated structures
  trachea, bronchi, and bronchioles (B) the lining of the whole of the digestive tract:
  oral cavity and tongue
  oral pharynx and laryngeal pharynx
  esophagus
  stomach
  small intestine
  large intestine, caecum, and appendix
  sigmoid colon and rectum
  anal canal (C) the lining of the whole of the urogenital tract:
  urethra, bladder, and ureters
  renal pelvis and renal calyces
  vagina, uterine cervix, uterus, and Fallopian
  vas deferens, seminal vesicles, ejaculatory (D) the conjunctiva and the lining of the tear (E) all exocrine glands and associated ducts that are located at least partially within one of the mucosal surfaces described above, or within the underlying submucosa.

This invention is especially useful for the treatment of diseases of Protista and parasitic origin, as defined above, particularly acne, malaria and other parasites or lesions resulting from parasites.

The term "parasite" includes parasites of humans and other animals, including parasitic protozoa (both intracellular and extracellular), parasitic worms (nematodes, trematodes, and cestodes) and parasitic ectoparasites (insects and mites).

The parasitic Protozoa include:
  malarial parasites of humans or other animals
    malarial parasites of humans
      *Plasmodium falciparum*
      *Plasmodium ovale*
      *Plasmodium malaria*
      *Plasmodium vivax*
  leishmanial parasites of humans and or other animals
    leishmanial parasites of humans
      *Leishmania tropica*
      *Leishmania major*
      *Leishmania aethiopica*
      *Leishmania brasiliensis*
      *Leishmania guyanensis*
      *Leishmania panamenis*
      *Leishmania peruviana*
      *Leishmania mexicana*
      *Leishmania amazonensis*
      *Leishmania pifanoi*
      *Leishmania garnhami*
      *Leishmania donovani*
      *Leishmania infantum*
      *Leishmania chagasi*
  trypanosomal parasites of humans and/or other animals
    trypanosomal parasites of humans
      *Trypanosoma cruzi*
      *Trypanosoma brucei gambiense*
      *Trypanosoma brucei rhodesiense*
  amoebic parasites of humans and/or other animals
    amoebic parasites of humans
      *Entamoeba histolytica*
      Naeglaria species
      Acanthamoeba species
      *Dientamoeba fragilis*
  miscellaneous protozoan parasites of humans or other animals
    miscellaneous protozoan parasites of humans
      *Toxoplasma gondii*
      *Pneumocystis carinii*
      *Babesia microti*
      *Isospora belli*
      Cryptosporidium
      Cyclospora species
      *Giardia lamblia*
      *Balantidium coli*
      *Blastocystis hominis*
      Microsporidia species
      Sarcocystis species Some of these miscellaneous protozoa cause self-limiting disease in normal people, but serious problems in HIV patients.

parasitic nematodes in humans and/or other animals
    parasitic nematodes in humans
      filarial nematodes
        *Wuchereria bancrofti*
        *Brugia malayi*
        *Brugia timori*
        *Onchocerca volvulus*
        *Loa loa*
        *Tetrapetalonema perstans*
        *Tetrapetalonema streptocerca*
        *Mansonella ozzardi*
        *Dirofilaria immitis*

*Dirofilaria tenuis*
  *Dirofilaria repens*
 intestinal nematodes
  *Ascaris lumbricoides* (roundworm)
  *Necator americanus* (hookworm)
  *Ancylostoma duodenale* (hookworm)
  *Strongyloides stercoralis* (threadworm)
  *Enterobius vermicularis* (pinworm)
  *Trichuris trichiura* (whipworm)
  Trichostrongylus species
  *Capillaria philippinensis*
 tissue nematodes
  *Trichinella spiralis*
  Anasakis species
  Pseudoterranova species
  *Dracunculus medinensis*
parasitic trematodes in humans and/or other animals
 parasitic trematodes in humans
  *Schistosoma mansoni*
  *Schistosoma haematobium*
  *Schistosoma japonicum*
  *Clonorchis sinensis*
  Paragonimus species
  Opisthorchis species
  *Fasciola hepatica*
  *Metagonimus yokogawai*
  *Heterophyes heterophyes*
  *Fasciolopis buski*
parasitic cestodes in humans and/or other animals
 parasitic cestodes in humans
  *Taenia saginata*
  *Taenia solium*
  Hymenolepis species
  Diphyllobothrium species
  Spirometra species
  Echinococcus species The method of this invention comprises the administration of ALA, other precursors of PpIX and other endogenous porphyrins, to the patient. The administration can also be in vitro as applied to tissues of the patient, i.e., ex vivo. In ex vivo methods, tissue containing the rapidly growing cells are removed from the patient, an effective amount of ALA or endogenous porphyrin is added thereto, then the preparation is subjected to photoactivating light, before being readministered to the patient. The amounts of ALA constituting an effective dose can be determined by one skilled in the art by analogy with the doses used for synthetic porphyrins, based on milligrams per kilogram body weight for in vivo systemic application and the typical concentrations for topical or ex vivo applications. The compound can be conveniently used orally or intravenously at a dosage of about 10 to 100 mg/kg per single dose, preferedly as a dosage of 40–50 mg/kg; however split dosages of 10 mg/kg four times per day may also be given. The compound can be used topically at a dose of between 2% to 100%, with 100% being dry powder. Ex vivo concentrations of the compound are used on cell suspensions in a range of 1–5 mM, with a preferred range of 1–2 mM; however, if serum is present, a higher dose of about 15 mM should be used. If ex vivo use on whole blood, the compound is used at about 15 mM; however, if an iron kelator, such as Desferol™ or des ferroxamine, a lower concentration may be used.

Thus, one application for the method of this invention is the detection and quantitation of parasites by ALA-induced fluorescence. The foregoing includes fluorescence flow cytometry of suspensions of cells or parasites ex vivo, fluorescence microscopy of cells, including but not limited to tissues, body fluids, fecal material in vivo or ex vivo, and quantative spectrophotofluorimetry of cells, including but not limited to tissues, body fluids, urine, or fecal material in vivo or ex vivo.

Another application for the method of this invention is the killing of parasites preferentially photosensitized by exposure to ALA or an endogenous porphyrin either in vivo or ex vivo. The conjunctiva, which can be treated either topically or systemically with ALA, followed by, after an appropriate period of time, exposure of the skin or conjuctiva to photoactivating light. The parasites can also be present in the peripheral blood, in which case the ALA can be administered systemically, followed by, after an appropriate time, which can be easily experimentally determined, exposing the defined area of the skin or the blood passing through a large vein to photoactivating light via an optical guide within a transparent catheter that has been inserted into the vein. Parasites located within one cm. of the surface of hollow organs that are accessible to fiberscopic examination (respiratory tract, digestive tract, urogenital tract, abdominal cavity, pelvic cavity, thoracic cavity) can be diagnosed or treated by systemic administration of the ALA, followed by, after the appropriate period of time, exposure of the surface of the target tissue via an appropriate light guide. Parasites located at sites that are not readily accessible to fiberscopic examination can be treated with the photoactivating light via a light guide that has been surgically introduced into the target area through a needle or following surgery.

Additional applications of the method of this invention are to detect very low levels of metabolically active malarial parasites in peripheral blood or marrow cell suspensions. Such detection can be used to screen banked blood or as a screening procedure for patients suspected to have viable malarial parasites. The screening method using ALA would be accomplished by flow cytometry.

Still another application for the method of this invention would be to distinguish between metabolically active ("viable") and inactive ("non-viable") malarial parasites to evaluate the response to therapy in patients infected with drug-resistant malaria more quickly than is now possible. Present methods for quantitating the level of parasitemia do not distinguish between viable and non-viable parasites. Thus, parasites that have been killed as a result of recent therapy may not be distinguishable from viable parasites. If the parasites are in fact resistant to the specific drug(s) that are being used for therapy, resistance to these drugs (as shown by failure to reduce the level of parasitemia) may not become obvious for some time after the initation of therapy.

In some cases it might be life-saving to recognize more quickly that a particular drug is not effective. Since ALA induces fluorescence only in plasmodia that are metabolically active, it is possible to distinguish between "viable" and morphologically similar "non-viable" malarial parasites in the peripheral blood. Drugs that fail to produce a decrease in the proportion of the erythrocytes that accumulate PpIX fluorescence when exposed to ALA in vitro could be identified quickly and replaced by other drugs that possibly might be more effective. The technology would not necessarily require flow cytometry, since relatively simple and much less expensive fluorometers could be used if the level of parasitemia is sufficiently high.

In cases of partially drug-resistant malaria in which there is a slow response to the drugs, it may be difficult to know when it is safe to discontinue therapy. Since ALA-induced PpIX fluorescence can detect viable plasmodia at very low levels of parasitemia, the technique might be used to verify that the parasitemia has been reduced to undetectable levels before maintenance therapy is discontinued. However, flow cytometry would be required for such low-level measurements.

The foregoing could also be used to screen in vitro for sensitivity/resistance of the plasmodia from a given patient to selected anti-malarial drugs, since ALA induces fluorescence only in plasmodia that are metabolically active.

Yet another application of this invention is the selectivel photosensitization and killing of malarial parasites in vivo or in vitro by exposing them to photoactivating light. The light would be transmitted to the malaria parasites in the circulating blood either through the skin, via an indwelling intravenous or intra-arterial catheter or by extracorporeal photodynamic therapy of blood, especially for patients who have failed to respond to other therapies, particularly those who might be considered candidates for a therapeutic exchange transfusion.

This invention is also particularly applicable to the treatment of fungal infections. Fungal infections are becoming of increasing importance in the past two decades due to the increasing number of immunocompromised patients, both by chemotherapy and diseases such as AIDS. Immunosuppression results in an increased incidence of fungal infections. Fungal infections can be divided into three categories: cutaneous, subcutaneous, and systemic. Cutaneous infections are by far the most prevalent. Fungal infections predispose their hosts to bacterial superinfections.

The method of the instant invention is carried out in the same manner as that for synthetic porphyrins previously reported. More specifically, the method of this invention is used to detect or treat rapidly growing cells exogenous to the body, including Protista cells and parasites.

The wavelength of the photoactivating light is of some importance, as it has been shown that between 1 and 10 percent of incident red light (600–700 nm) can pass through a slab of human tissue 1 cm thick, whereas only 0.001 percent or less of blue light (about 400 nm) can pass through the same thickness of human tissue. The photosensitizer will, therefore, be more successful if it absorbs red light. PpIX does strongly absorb red light. The present approach has several advantages over the prior art. First endogenous PpIX has a much shorter half-life in normal tissues (human and mouse, at least) than does HpIX, HpD or Photofrin® II. This greatly reduces the danger of accidental phototoxic skin reactions in the days following treatment. Second, the ALA can be applied topically to certain types of lesions. This improves the specificity of the treatment, reduces the danger of accidental phototoxic reactions to a very low level, and greatly reduces the amount of both ALA and PpIX to which the entire body would be exposed if an equally effective dose of ALA were to be given systemically.

Both ALA and PpIX are normal products of metabolism, and are handled quite readily by the biochemical machinery of the body. However, since very large doses of ALA (like large doses of HpIX or HpD) are associated with a transient decrease in motor nerve conduction velocity, it is desirable to reduce the dose of ALA to the minimum that is still effective. Topical application requires much less ALA than systemic administration. Third, PpIX is rapidly inactivated by the photoactivating light. Following exposure of tissues containing PpIX to a therapeutic dose of photoactivating light, there is a substantial decrease in photosensitization of the tissues within the treatment volume. Consequently, if PpIX is induced by the topical application of ALA to specific lesions, the patient can be exposed to sunlight immediately post-treatment without danger of serious phototoxicity. Also, the dosimetry of the photoactivating light is great simplified. Fourth, ALA is an effective inducer of PpIX when given by mouth, by topical application, or by injection. In contrast, HpIX, HpD and Photofrin II are effective in most situations only when given by injection. The versatility of ALA enhances its acceptability for routine use by the medical profession, since the oral and topical routes of administration are much more convenient than the parenteral. Fifth, the normal and abnormal tissues that can be photosensitized by the administration of ALA are somewhat different from those that can be photosensitized by the administration of HpIX, HpD or Photofrin II. Consequently, ALA would be useful in clinical situations in which the other photosensitizers are not.

Thus the present technique is not merely another way to do what can be done already but is, in fact, a significant advance in therapeutic capability.

Without further elaboration, it is believed that one skilled in the art can, using the preceding description, utilize the present invention to its fullest extent. In carrying out the method of this invention, the quantities of materials utilized are not in themselves critical and can be varied within the scope and spirit of the invention. The following examples are merely illustrative of preferred embodiments and not intended to be limitative of the remainder of the disclosure in any way whatsoever.

EXAMPLE 1

Long Term Photodynamic Endometrial Ablation

Rats were divided into 2 groups (6 and 7 rats/group) and their uterine horns were injected with 4 or 8 mg ALA. Example 1, of U.S. application Ser. No. 08/082,113, filed Jun. 21, 1993 (U.S. Pat. No. 5,422,093), was repeated with the exception that all rats were exposed to light and the time from ALA administration to breeding was extended from 10–20 days to 60–70 days. All other procedures were identical to Example 1.

Breeding 60–70 days after photodynamic treatment with 4 mg ALA resulted in no implantations in the uterine horns treated with ALA (n=6) whereas fetuses were found in all control uterine horns treated with saline (n=6). These results confirmed the long term endometrial ablative effect of PDT. In the groups of rats (n=7) treated with 8 mg ALA 2 of 7 became pregnant in ALA treated uterine horns compared with 7 of 7 pregnancies in the saline treated horns.

Histology

In order to show normal uterine histology of a nonpregnant uterine horn contralateral to a pregnant uterine horn one uterine horn was ligated at its distal end prior to breeding. At gestation of 10–15 days nonpregnant uterine horns were harvested and histologically processed. The uterine mucosa was lined with columnar epithelium and there was hypertrophic infolding of endometrial tissue with tortuous glands. In contrast, prior photodynamic treatment with ALA consistently resulted in an atrophic endometrium despite the hormonal stimulus of the contralateral pregnancy.

EXAMPLE 2

The procedures of Example 1 (U.S. Pat. No. 5,422,093) were repeated with 1, 2, 3, 4 and 5 hour incubation periods using a level of 1 mM of ALA. No significant fluorescence was observed in the myometrial samples or in the endometrial samples incubated for 2 hours. Maximum fluorescence was observed in the endometrial samples incubated for 4 hours.

EXAMPLE 3

Endometrial Fluorescence in vivo Following Topical Application of ALA in the Non-Human Primate 50 mg of ALA was injected into the uterine lumen of an adult, healthy, female rhesus monkey following exposure of the uterus at laparotomy. A hysterectomy was performed 3 hours later and cross sectional slices incorporating endometrial and myometrial tissue were taken from the uterine specimen. These slices were subjected to examination by fluorescence microscopy as in Example 2 and 3 above. Fluorescence was observed throughout the endometrium of all slices. No fluorescence was observed in the myometrium.

The above examples clearly illustrate that endometrial ablation in a range of animal species, including humans, by photodynamic therapy using ALA can be achieved with little or no damage to the underlying myometrial tissues.

EXAMPLE 4

Detection or Treatment of Yeast and Fungi

A. In Vitro Studies

Clinical isolates of *Candida albicans, Candida glabrata*, and *Cryptococcus neoformans* and environmental isolates of Penicillium species, *Aspergillus niger, Aspergillus fumigatus*, and Alternaria species and *Saccharomyces cerivisiae* (brewer's yeast) obtained from the clinical microbiology laboratories of Kingston General Hospital, Kingston, Ontario, Canada were used. The organisms were plated, and during rapid growth were treated with various concentrations of ALA varying from 1 mM to 100 mM by flooding or by using diffusion wells in the agar, while the isolates of Penicillium and Aspergillus were treated with 40% or 80% solutions of ALA in water and the Penicillium species, Alternaria species, *Aspergillus niger* and *Aspergillus fumigatus* were treated with 20% ALA in water via diffusion wells. Treatment of the various fungi resulted in fluorescence emission peaks that showed the characteristics of PpIX. Positive PpIX accumulation occurred in both molds and yeasts.

B. In Vivo Studies

The procedure of Giger et al. Infection and Immunity 19 (2) 499–509 (February 1978) was used with the following modifications. A clinical specimen of *C. albicans* was replated in blood agar so it was actively growing and left at room temperature for 72 hours. The sample was suspended in TSB to McFarland 0.5 turbidity after which a 1.0 ml sample was inoculated into an aerobic culture bottle and left shaking for 24 hours on a 37° C. rotor shaker. A 10 ml sample was withdrawn and centrifuged at 70,000 rpm for 10 minutes to separate the cells from the media. The supernate was discarded and the pellet resuspended in 10 ml of TSB. Serial dilusions ($10^{-1}$ to $10^{-5}$) were made in and replicated twice on agar and left to incubate for two days at 37° C. The McFarland 1.0 sample was centrifuged and the pellet resuspended in 1.0 ml buffer for injection.

On day zero an intradermal injection of the *C. albicans* suspension (about $7 \times 10^6$ organisms/ml saline) was made into the right flank of 5 adult hairless mice. The amount was just enough to make a small vesicle under the skin. Lesions form by day 2. Later, some mice were given a second injection on the opposite side.

Three hours prior to their sacrifice, the mice were given 240 mg/kg ALA (10 mg/ml) by intraperitoneal injection, with the exception of mouse #3 which was used as a control. Fluorescence emission spectra on the live mice were taken every 15 minutes (mouse #1 readings every 20 minutes) for 3 hours after injection on each lesion, and at various control areas of the mice—neck skin flap and lateral side opposite the lesion on mouse 5. Three hours after the injection of ALA the mice were sacrificed and the lesions were excised. The lesions in mice 1, 2, 3, and 4 were frozen in 2-methylbutane cooled to the temperature of liquid nitrogen. The frozen lesions were sectioned and slides were prepared for spectral analysis or fluorescence microscopy, H and E staining for histology, and Grocott silver stains for fungi identification.

Primary and secondary lesions showed increased PpIX accumulation relative to the control mice.

EXAMPLE 5

(1) Selective Induction of the Synthesis and Accumulation of Protoporphyrin IX and/or Other Endogenous Porphyrins Within Parasites in vivo or in vitro.

In vivo—If the parasites in question involve the skin, conjunctiva, oral mucosa, nasal mucosa, anal mucosa, or urothalium, ALA may be applied directly to the surface of the affected tissue. If the parasites are located at sites that are not suitable for topical application, an effective amount of ALA is administered systemically, either by mouth, by subcutaneous injection, or by intravenous injection.

In vitro—The material suspected of containing parasites is incubated under appropriate conditions in the presence of an effective concentration (generally around 5 mM) of ALA.

EXAMPLE 6

In vivo Studies

The injection of an effective dose of 5-aminolevulinic acid (ALA) into mice infected with *P. yoelii* leads to the accumulation of fluorescing and photosensitizing concentrations of protoporphyrin within metabolically active parasites. There is no such accumulation of protoporphyrin within non-viable parasites, or within normal erythrocytes or leukocytes. In parasitized erythrocytes, the protoporphyrin accumulation is localized to the parasite itself.

Metabolically active (viable) malarial parasites can be distinguished readily from parasites that are inactive (dead), since only parasites that are metabolically active can synthesize protoporphyrin. In addition, metabolically active (viable) malarial parasites can be killed selectively by exposing infected blood or cell suspensions to photoactivating wavelengths of light. This procedure causes no significant damage to the accompanying normal erythrocytes and leukocytes, since they do not accumulate enough protoporphyrin to become photosensitized.

EXAMPLE 7

Demonstration, Quantification, and Analysis of ALA-Induced Fluorescence Within Erythrocytes Parasitized by *P. yoelii*

Normal mice were given intraperitoneal injections of blood or spleen cells obtained from mice infected with *P. yoelii*. When the malaria was well established, some of the infected mice were given a single intraperitoneal injection of 250 mg of ALA per kg of body weight. Controls included infected mice that were not given ALA, and non-infected mice that were given/not given ALA.

At various intervals thereafter, suspensions of blood and/or spleen cells were examined by the following techniques.

Fluorescence Microscopy: Red fluorescence developed within parasitized erythrocytes of mice given ALA, but not within any of the controls. This fluorescence was localized to the plasmodia.

Fluorescence Flow Cytometry: Large numbers of erythrocytes in suspensions of cells from the peripheral blood and spleen of heavily parasitized mice given ALA developed red fluorescence. Cells from the control mice were uniformly negative. This technique permitted the rapid detection and enumeration of erythrocytes that contained metabolically-active parasites, and produced relative values for the intensity of ALA-induced fluorescence in such erythrocytes.

Spectrophotofluorometry: Blood and spleen cells from heavily parasitized mice given ALA were washed and pelleted by centrifugation. Protoporphyrin was the only fluorophore that was identified by spectrophoto-fluorometry. As expected, cell pellets from the control animals contained only traces of protoporphyrin.

Demonstration and Quantitation of ALA-Induced Photosensitization of the Intra-Erythrocytic Stage of P. yoelii.

Normal mice were given intraperitoneal injections of blood or spleen cells obtained from mice infected with P. yoelii. When the malaria was well established, some of the infected mice were given a single intraperitoneal injection of 250 mg of ALA per kg of body weight. Controls included infected mice that were not given ALA, and non-infected mice that were given/not given ALA.

At various intervals thereafter, suspensions of blood and/or spleen cells were exposed to graded doses of photoactivating light. Light-induced loss of viability of the P. yoelii was demonstrated by (a) loss of infectivity, or (b) loss of ability to accumulate the fluorescent cleavage product of calcein-AM.

(A) Infectivity Assay: Mice infected with P. yoelii were given a standard dose of ALA by intraperitoneal injection. Peripheral blood and/or spleen cells were collected after a standard interval, exposed to standard doses of photoactivating light (including a no-light control) and then injected into normal mice. If the control (no-light) mice developed malaria and died while the mice given cells that had been exposed to a given dose of light remained free of malaria and lived indefinitely, this was considered to be evidence that the light treated cell suspensions did not contain enough viable plasmodia to cause an infection.

For example, a Balb/c mouse with advanced malaria (P. yoelli) was given an intraperitoneal injection of 250 mg of ALA per kg of body weight. Four hours later, its spleen cells were suspended in isotonic saline. Half of the spleen cell suspension was placed on ice and ekxposed to photoactivating light (waveband 600–700 nm, intensity 100 nW/cm$^2$, total dose 540 J/cm$^2$), while the other half was kept on ice in the dark. Balb/c mice were injected intraperitoneally with either the light treated or untreated sample. Survival of the mice was followed for 90 days. FIG. 1 illustrates the duration of survival of individual mice following the injection of spleen cells infected with P. yoelii.

(B) Photosensitization studies (Ex vivo studies, direct photoradiation): A group of 4 hairless female mice were used. Two mice were infected with P. yoelii and 2 other mice were non-infected. Mice infected with malaria were usually in the 8th day following inoculation with plasmodia. Mice were divided in two groups: one group was treated with ALA, the control group was not treated with ALA.

Both groups were then kept in the dark for a period of 3 hours. Mice were then sacrificed (overdoses of chloroform) and infected blood cells were obtained from homogenized spleen. Spleens were homogenized in 3 cc of isotonic saline solution. From this homogenization 1 cc was taken and diluted in 24 cc of isotonic saline solution, then from this dilution 1 cc was taken and placed in test tubes (a total of 8 tubes). Four tubes were kept in dark and four tubes were photoirradiated.

The source of light was a tungsten lamp with a filter for red light (600–700 nm). The beam was 10 cm in diameter and the fluence about 70 mW/cm$^2$. The samples were placed in ice on a turntable (33 rpm) to assure a uniform distribution of the light in the target cells.

To determine the viability of the plasmodium after being irradiated, the contents of each tube were inoculated into hairless mice, and then the mice were followed for survival.

Control groups for light alone but not ALA, and ALA but not light, were also used to make sure that photsensitization was due to ALA plus light.

(C) Spectrophotofluorimetric studies: A group of 8 hairless 1 female mice were used. Four mice were in the 8th day post inoculation with Plasmodium yoelii with 35% parasitemia and 4 normal mice were normal (non-infected). The mice were divided into 4 groups of two mice in each.

i) 2 infected mice were given an IP injection of 250 mg/kg of ALA in PBS.

ii) 2 normal (non-infected) mice were also injected IP with 250 mg/kg of ALA in PBS.

iii) 2 reference controls were included: 2 infected mice with malaria and 2 non-infected mice, none received ALA. All 4 groups were kept at normal room temperature, in the dark, for 4 hours and then sacrificed. Mice were anesthetized with chloroform and then blood was collected by cardiac puncture (heparinized syringe with 20 G 1' needle). Approximately 0.9 cc blood was collected and transferred to a 5 cc test tube, kept on ice and in the dark. Test tubes were then centrifuged for 10 minutes. Using a spectrophotofluorometer set for excitation at 410 nm and fluorescence emission at 635 nm., fluorescence measurements were taken of the supernant and the pellet.

Hemolysis with 1% saponin was carried out in samples after the first fluorescence measurements, and the free Plasmodia are centrifuged to form a pellet. Then fluorescence measurements were taken from the pellet and the supernant. Protoporphyrin fluorescence was detected only in Plasmodial pellet derived from infected mice given ALA.

(D) Flow cytometer studies (Pharmacokinetic studies): A group of 4 hairless female mice were used. Two mice were infected with P. yoelii and 2 other mice were not infected. Mice infected with malaria were usually in the 8th day post inoculation with the infected plasmodia. ALA was given directly to the mice (250 mg/kg intraperitoneal), then 2 drops of whole blood were withdrawn at regular intervals of time from the tail of each mouse and placed in 5 cc flow cytometer test tubes containing 0.5 cc of RPMI 1640 and then analyzed by the flow cytometer to follow accumulation of PpIX. Only infected mice given ALA developed fluorescence in their erythrocytes.

For the in vitro studies, no ALA was given to the donor mice. Two drops of whole blood were withdrawn from the tail of each mouse and placed in a 35 mm petri dish containing 3 cc of RPMI 1640 without phenol red.

i) a petri dish contained infected whole blood with 5 nM ALA in RPMI.

ii) a second petri dish contained infected whole blood plus RPMI but not ALA.

iii) a third petri dish contained normal whole blood cells with 5 mM ALA in RPMI.

iv) a fourth petri dish contained normal whole blood cells with RPMI but not ALA.

All petri dishes were incubated at 37 Celsius and room air environment. Samples (0.5 cc) were taken at regular intervals from these incubated petri dishes to be analyzed in the flow cytometer to follow accumulation of PpIX. Only cells from infected mice developed PpIX fluorescence when incubated with ALA.

Application of ALA-Induced PpIX PDT to the Treatment of Malaria.

Malaria is caused by infection of the host with unicellular parasites known as plasmodia. At one stage in their life cycle, the plasmodia infect and develop within erythrocytes of the peripheral blood, spleen, and/or marrow. They may infect the liver and certain other organs also.

Of the numerous species of plasmodia that have been identified, only a few can infect humans. Plasmodia that cause malaria in mice but not humans provide a safe and convenient model for laboratory studies of malaria.

These examples involve the murine malarial parasites *Plasmodium yoelii* (lethal strain) and *Plasmodium chabaudi* (non-lethal strain) as models for human malaria.

In vivo Photosensitization

When mice infected with the murine malarial parasites *P. yoelii* or *P. chabaudi* were given an adequate dose of 5-Aminolevulinic Acid (ALA) by intraperitoneal injection, what appeared spectroscopically to be protoporphyrin (PpIX) accumulated in many of the plasmodia within erythrocytes of the peripheral blood, spleen, and marrow. However, significant concentrations of PpIX did not accumulate within the non-infected erythrocytes or within the great majority of the leukocytes in the infected mice.

a fluorescent material that may have been a complex of protoporphyrin with a light metal (perhaps zinc protoporphyrin) sometimes accumulated in association with the PpIX.

following exposure to an adequate dose of light of wavelengths within the photoactivation spectrum of PpIX, the plasmodia that had been exposed to ALA lost their normal ability to accumulate calcein when exposed to calcein-AM, and also lost their ability to cause malaria when injected into recipient mice. However, the non-infected erythrocytes and the leukocytes in the same cell suspensions showed no morphological evidence of damage following exposure to the photoactivating light.

In vitro Photosensitization

When peripheral blood, spleen, or bone marrow cells from mice infected with the murine malarial parasites *P. yoelii* or *P. chabaudi* were incubated under suitable conditions in the presence of an effective concentration of ALA, what appeared spectroscopically to be protoporphyrin (PpIX) accumulated within many of the plasmodia in erythrocytes of the peripheral blood, spleen, or marrow. However, significant concentrations of PpIX did not accumulate within the non-infected erythrocytes or within the great majority of the leukocytes in the infected mice.

The exposure of metabolically active *P. yoelii* or *P. chabaudi* to an effective concentration of ALA under suitable conditions in vivo or in vitro leads to the preferential accumulation of fluorescing and photosensitizing concentrations of PpIX in those plasmodia, but not in non-infected erythrocytes or in the great majority of the leukocytes in peripheral blood, spleen, or bone marrow cell suspensions.

Plasmodia-specific ALA-induced fluorescence can be used to detect and quantitate metabolically active malarial parasites in suspensions of cells from peripheral blood, spleen, or marrow.

Plasmodia-specific ALA-induced photosensitization can be used to destroy malarial parasites selectively, by exposing them in vitro or in vivo to an adequate dose of photoactivating light.

EXAMPLE 8

Acne

Acne is an inflammatory follicular papular and pustular eruption involving the skin. The treatment of acne using the method of the instant invention would be considered to be the treatment of either (a) endogenous lesions of the sebaceous apparatus of the skin due to intrafollicular hyperkeratosis or (b) exogenous bacteria cells present in the acne lesions, particularly Propionibacterium (Corynebacterium) acne.

Evaluation of PpIX induced fluorescence in 8 subjects with mild to moderate truncal acne was performed. Bacterial infections are frequently associated with lesions of acne, e.g., *P. acne*. Following evaluation of baseline acne lesion fluorescence, ALA solution 10 and 20% was applied to 10 5 cm$^2$ sites on the chest or back of volunteers and evaluated at times 0, 3, 8 and 24 hours after ALA application. One site of each concentration was also occluded with opaque film for 3 hours and evaluated at similar time points for comparison with unoccluded sites. Fluorescence of both acneiform lesions as well as surrounding normal skin was assessed visually using a 4 point grading system (0=none, 4=extremely severe) and documented photographically.

In all subjects, unoccluded sites had a gradual increase in PpIX fluorescence that was dose dependent, maximum at 8 hours, specific for acne lesions and spared normal surrounding skin. These sites had weak or no fluorescence by 24 hours. Little difference in fluorescence intensity was noted by lesion type (cornedones vs papules vs pustules) in the same subject, however, time to maximal fluorescence and maximal fluorescence intensity was variable from subject to subject. Lesions with surrounding erythema (larger papules and pustules) developed fluorescence extending to the clinical limit of erythema. Vehicle control sites remained at baseline. In contrast, occluded sites developed PpIX fluorescence in both acne lesions and normal surrounding skin that persisted longer than unoccluded sites and remained present at 24 hours.

EXAMPLE 9

Cutaneous Fungal Infections

Historically, fungal infections have not attracted as much attention as bacterial infections. This focus of research has been due to a number of factors, most notably, the high incidence, the degree, and the effect of bacterial infections in humans. However, this trend has changed in the past couple of decades. With the increasing number of immunocompromised patients, both by iatrogenic (chemotherapy) and disease (AIDS) causes, the incidence of fungal infections has increased. This has coincided with an increase in the morbidity and mortality rates due to fungal infections in the last decade.

Fungal infections can be divided into three categories: cutaneous, subcutaneous and systemic. While the systemic infections (blastomycosis, candidiasis, etc.) have more serious sequelae, the cutaneous infections are much more prevalent. Between 1971 and 1974, fungal infections had a reported rate of 88/1000 persons in the U.S. with the non-invasive cutaneous infections responsible for 90% of the cases. (This is the number of reported cases. Because of the non-life threatening sequelae of cutaneous infections, the actual incident rate is likely much higher.) They were also cited as the most common skin infection.

Cutaneous infections can be further divided into three sub-categories: superficial, dermatophytoses and dermatomycoses. Superficial infections do not penetrate the outer layer of the skin and do not involve either the hair or nails. Tinea nigra, black piedra and white pedra are examples of superficial fungal infections. Dermatophytoses are infections of the skin, hair, and nails, and include all layers of the stratum corneum. These infections are caused by dermatophytes, fungi which rarely cause disseminated infections. These organisms release keratinases, which likely explains their localization within the keratinized tissues. These fungi cause little mortality, but are a major cause of morbidity worldwide, and in North America a major expenditure of time and money. These infections predispose their hosts to bacterial superinfections. Dermatomycoses are cutaneous infections caused by non-dermatophytes and have a greater chance of invasion and dissemination (e.g. superficial candidiasis, mycetoma, sporotrichosis), especially in an immunocompromised host. However, as stated before, the greater majority of fungal infections are caused by the non-invasive dermatophytes.

Dermatophytes

Dermatophytes include Trichophyton spp., Microsporum spp. and Epidermophyton spp. genera. Ecologically, these fungi are anthrophilic (human to human transmission), zoophilic (animal to human transmission) and geophilic (soil to human transmission, possibly via an animal intermediary). Typically the anthrophilic fungi cause little inflammation (increasing the likelihood of chronic infection) and the zoophilic fungi cause a furuncular reaction.

Dermatophytoses are named "tinea" followed by the body location (e.g., tinea capitis is an infection of the head). Table 1 lists the dermatophytoses and their causative dermatophyte as found in a survey of dermatological visits by U.S. Army personnel. This data has been supported by data collected from surveys of students, inmates, and other armed forces personnel in the U.S. The most common dermatophyte worldwide is *T. rubrum* (survey of major dermatologic centers).

TABLE 1

Incidence of Dermatophytoses and the Causative Dermatophytes

| Dermatophytoses | Incidence | Most common Dermatophytes (in L to R) |
|---|---|---|
| tinea pedis | 44% | T. mentagrophytes, T. rubrum |
| tinea unguium | 16% | T. rubrum, T. mentagrophytes, E. floccosum |
| tinea cruris | 15% | T. rubrum, T. mentagrophytes, E. floccosum |
| tinea corpis | 13% | T. Rubrum |
| tinea barbae | 4% | T. mentagrophytes, T. verrucosum |
| tinea capitis | 3% | T. tonsurans, M. canis |

Clinical Presentation

These infections are not life threatening but they can cause a significant amount of discomfort. Typically they cause scaling, fissuring, peeling, itching, burning erythema, and in some circumstances, maceration. *Tinea capitis* usually causes reversible hair loss. *T. mentagrophytes* and *T. verrucosum* can produce a violent inflammatory reaction. As well, these infections are not pretty and can have serious aesthetic consequences. The outcome of these infections is either a spontaneous cure, a cure by medication, a treatable chronic condition, or a persistent infection despite medication. Both the presentation and outcome is a function of the dermatophyte virulence and the host's defense capabilities. Immunocompromised individuals invariably fare worse than their immunocompetent counterparts.

Treatment

Dermatophytoses can be treated topically or orally. The advantage of treating topically is that more aggressive (toxic) therapy can be employed, whereas orally, less toxic drugs are required. However, topical drugs can cause itching, burning, redness, and sensitization of the infected area. Oral therapy has the advantage of gaining access to tissue sites normally unattainable to topical therapy (i.e. the nail beds). To gain access to the site of action, both routes must overcome the body's natural defenses to foreign molecules since none of the drugs used are endogenous molecules. The imidazoles and triazoles are used topically and ketoconazole and griseofulvin orally. However, ketoconazole has a large number of side effects, especially if used for a long period of time, and *T. rubrum* and *T. tonsurans* have shown resistance to therapy. Both oral regimens require careful monitoring and some patients may not be treated because of contraindications.

Antifungal therapy depends on the thickness of the site infected. Tinea cruris and corpis require a shorter treatment time than tinea manum and tinea pedis because the skin is thinner in the groin and on the body as compared to the hands and feet. Infections localized to the hair follicle roots require 4 to 6 weeks of treatment (root=3–4 mm under the skin surface, at 1 mm/week growth). The fingernails require 4–9 months of treatment, and the toenails, which grow even slower, require 9–18 months of treatment. Due to wearing shoes, the feet and toenails are also subjected to an environment which is conductive to fungal growth (warm, moist), making it more difficult to eliminate the infection.

Tinea unguium or onychomycosis has been particularly troublesome to treat. Treatment regimens can last as long as 18 months, with considerable time and money invested in the cure. Nail avulsion (removal) is often included in the regimen but may cause considerable postoperative discomfort. Even so, only a 75–80% cure rate can be obtained with fingernail infections. The results are more bleak for toenail infections (25% cure rate). If more than one nail is involved, a permanent cure is unlikely. It has been estimated that at least 15–20% of the U.S. population between the ages of 40–60 have onychomycosis.

Clinical Application of ALA-Induced Photosensitization to Chronic Toenail Infection with Dermatophyte (Trichophyton Species)

An adult male presented with a chronic dermatophytic infection involving the nail of the great toe. The nail itself was badly deformed as a result of the infection. The surrounding tissues showed evidence of chronic low-grade inflammation.

A 20% (w/w) solution of 5-aminolevulinic acid (ALA) in an oil-in-water emulsion (Glaxal Base) was applied to the toenail and surrounding tissues, and then covered with a water-resistant plastic dressing (Tegaderm). Four hours later, the Tegaderm and residual cream were removed and the whole area exposed to photoactivating (red) light.

The patient experienced a typical subjective response while the toe was being exposed to the light—itching, stinging, and a sensation of mild burning. Upon completion of treatment, the toe was erythematous and somewhat edematous. This gradually decreased over the next few days.

Over the next few months, all clinical evidence of the fungal infection vanished. The toenail is now growing without deformity.

EXAMPLE 10

The following organisms accumulate fluorescing and/or photosensitizing concentrations of PpIX when exposed to exogenous ALA:

(1) Protozoa
    (a) Leishmania—*L. donovani*
        [ALA-induced fluorescence]
    (b) Malaria—*Plasmodium yoelii*
        [ALA-induced fluorescence]
        [ALA-induced photosensitization]
        *Plasmodium chaubadi*
        [ALA-induced fluorescence]
        [ALA-induced photosensitization]
(2) Worms
    (a) Nematodes—*Lumbricus terrestris* (dewworm)
        [ALA-induced fluorescence]
        [ALA-induced photosensitization]
        *Enterobius vennicularis* (pinworm)
        [ALA-induced fluorescence]
        [ALA-induced photosensitization]

*Plasmodium yoelii* is a malarial parasite that can infect and grow progressively to produce a lethal form of malaria in susceptible strains of mice and rats. The inventors have found that, when normal mice are injected with standard numbers of blood or spleen cells obtained from donors infected with *P. yoelii*, they die of malaria 10 to 20 days after such injection. This mouse model is applicable to the study of malarial infections in humans, including *P. vivax, P. falciparum, P. malariae*, and *P. ovale*.

What is claimed is:

1. A method for treating in a human patient a non-malignant hyperproliferative skin lesion that preferentially accumulates a photoactivatable porphyrin, comprising administering to said human patient in need thereof an effective amount of a precursor of protoporphyrin IX thereby accumulating therapeutic levels of said protoporphyrin IX, and thereafter exposing said skin lesion to light capable of photoactivating said protoporphyrin IX.

2. The method of claim 1 wherein said precursor of protoporphyrin IX is administered topically.

3. A method for detecting in a human patient a non-malignant, hyperproliferative skin lesion that preferentially accumulates a photoactivatable porphyrin, comprising administering to said human patient in need thereof an effective amount of a precursor of protoporphyrin IX thereby accumulating detectable levels of said protoporphyrin IX, and thereafter exposing said skin lesion to light capable of photoactivating said protoporphyrin IX.

4. The method of claim 3 wherein said precursor of protoporphyrin IX is administered topically.

5. The method of claim 1 wherein said precursor is 5-aminolevulinic acid.

6. The method of claim 3 wherein said precursor is 5-aminolevulinic acid.

7. A method of treating a non-malignant, hyperproliferative skin lesion in a human patient in which protoporphyrin IX is produced from 5-aminolevulinic acid, comprising exposing said skin lesion in said human patient to a wavelength of light within the photoactivating spectrum of protoporphyrin IX.

8. A method of treating a non-malignant, hyperproliferative skin lesion in a human patient in which protoporphyrin IX is produced from 5-aminolevulinic acid, comprising exposing said skin lesion in said human patient to a wavelength of light within the photoactivating spectrum of protoporphyrin IX, wherein said light is generated using an artificial light source.

9. A method according to claim 7, wherein said light is only within the absorption spectrum of protoporphyrin IX.

10. A method according to claim 7, wherein said wavelength of light is limited to the group of wavelengths consisting of 350 to 700 nanometers.

11. A method according to claim 7, wherein the photoactivating light is limited to the red and blue regions of the spectrum.

12. A method of treating a non-malignant, hyperproliferative skin lesion, comprising (a) administering to a human patient a compound that induces accumulation of protoporphyrin IX in said skin lesion and then (b) exposing said skin lesion to a wavelength of light within the photoactivating spectrum of protoporphyrin IX.

13. A method according to claim 12, wherein said wavelength of light is generated using an artificial light source.

14. A method according to claim 12, wherein said wavelength of light is limited to the group of wavelengths consisting of 350 to 700 nanometers.

15. A method according to claim 12, wherein the photoactivating light is limited to the red and blue regions of the spectrum.

* * * * *